(12) United States Patent
Rontal (10) Patent No.: US 10,758,667 B2
(45) Date of Patent: Sep. 1, 2020

(54) BALLOON IRRIGATION AND CLEANING SYSTEM FOR INTERIOR WALLS OF BODY CAVITIES

(71) Applicant: Michael Rontal, Farmington Hills, MI (US)

(72) Inventor: Michael Rontal, Farmington Hills, MI (US)

( * ) Notice: Subject to any disclaimer, the term of this patent is extended or adjusted under 35 U.S.C. 154(b) by 590 days.

(21) Appl. No.: 14/172,393

(22) Filed: Feb. 4, 2014

(65) Prior Publication Data
US 2014/0221980 A1 Aug. 7, 2014

Related U.S. Application Data

(60) Provisional application No. 61/760,468, filed on Feb. 4, 2013.

(51) Int. Cl.
*A61M 3/02* (2006.01)

(52) U.S. Cl.
CPC ........ *A61M 3/0295* (2013.01); *A61M 3/0254* (2013.01); *A61M 3/0283* (2013.01)

(58) Field of Classification Search
CPC .... A61M 2025/1086; A61M 2025/105; A61M 2210/0618; A61M 29/02; A61M 2025/1052; A61M 25/1002; A61M 25/0075; A61M 25/007; A61M 2025/1031; A61M 2025/1047; A61M 2210/0681

See application file for complete search history.

(56) References Cited

U.S. PATENT DOCUMENTS

| | | | | |
|---|---|---|---|---|
| 5,653,690 A | * | 8/1997 | Booth | A61M 25/04 604/103.07 |
| 5,693,014 A | * | 12/1997 | Abele | A61M 25/1002 604/103.08 |
| 5,827,229 A | * | 10/1998 | Auth | A61B 17/22 604/164.13 |
| 7,361,168 B2 | | 4/2008 | Makower et al. | |
| 7,654,997 B2 | | 2/2010 | Makower et al. | |
| 8,114,062 B2 | | 2/2012 | Muni et al. | |
| 8,317,816 B2 | * | 11/2012 | Becker | A61M 25/10 606/196 |
| 8,708,986 B2 | * | 4/2014 | Shapland | A61M 1/0031 604/103.07 |
| 2006/0063973 A1 | * | 3/2006 | Makower | A61B 1/00135 600/114 |
| 2007/0073269 A1 | * | 3/2007 | Becker | A61M 3/0295 604/509 |
| 2007/0129751 A1 | | 6/2007 | Muni et al. | |

(Continued)

*Primary Examiner* — William R Carpenter
(74) *Attorney, Agent, or Firm* — John G. Posa (57) ABSTRACT

A method and apparatus for cleansing the interior surfaces of body cavities employs a balloon catheter adopted to be inserted into a cavity through its ostium with the balloon in collapsed condition. An input flow tube for a cleansing and/or medicating fluid passes through a central passage in the balloon. When the balloon is inflated to establish a narrow passage between the balloon and the cavity walls, a pressurized flow of the fluid is pumped out the distal end of the input flow tube through the passage, parallel to the cavity walls, where it scours the inner wall of the cavity, removing debris as it flows out of the ostium. The fluid flow is urged toward a turbulent condition by attachments to the outer wall of the balloon.

11 Claims, 6 Drawing Sheets

(56) References Cited

U.S. PATENT DOCUMENTS

| | | | | |
|---|---|---|---|---|
| 2007/0282255 A1* | 12/2007 | Salemi | .................. | A61M 25/04 |
| | | | | 604/96.01 |
| 2008/0015540 A1* | 1/2008 | Muni | ..................... | A61B 17/24 |
| | | | | 604/500 |
| 2008/0183128 A1* | 7/2008 | Morriss | ............... | A61M 3/0283 |
| | | | | 604/35 |
| 2009/0054837 A1* | 2/2009 | Von Holst | ............... | A61L 29/16 |
| | | | | 604/103.08 |
| 2010/0249702 A1* | 9/2010 | Magana | ............. | B23K 26/4065 |
| | | | | 604/103.01 |
| 2013/0116655 A1* | 5/2013 | Bacino | ........... | A61B 17/320725 |
| | | | | 604/509 |

* cited by examiner

BALLOON IRRIGATION AND CLEANING SYSTEM FOR INTERIOR WALLS OF BODY CAVITIES

CROSS-REFERENCE TO RELATED APPLICATIONS

This application claims the benefit of U.S. Provisional Application 61/760,468 filed on Feb. 4, 2013, the contents of which are incorporated herein by reference.

FIELD OF THE INVENTION

This invention relates to a method and apparatus useful to clean, scrub, debride or irrigate, the interior surfaces of body cavities and more particularly to such a method and apparatus employing a balloon-like inflatable catheter.

BACKGROUND OF THE INVENTION

Balloon catheters have been employed to provide treatment to relatively inaccessible body cavities such as occluded blood vessels, nasal cavities, wounds, or paranasal sinuses and the like. In some cases, these balloons are used to introduce fluids onto the linings of various body cavities to carry medications such as antibiotics and the like into intimate contact with the interior surfaces of the cavities. Attempts to clean a cavity with a forceful jet into the cavity that is filled with fluid is defeated as its force is absorbed by the fluid. A device that reduces the volume of the cavity to a thin rim over the entire surface can force the flow directly onto the walls and in a direction that parallels the walls but without dissipation of the force and covering the entire surface. In essence this is the basic concept of this invention.

Certain of these balloons have been formed with walls of porous materials so that the fluids from the interior of the balloons will flow outwardly against the body cavity interior surfaces to provide medicated fluids or the like to those surfaces. U.S. Patent Publication 2007/0129751 assigned to Acclarent, Inc. discloses a device for balloon sinusplasty which may employ a balloon with porous walls to deliver fluids to the interior walls of sinus cavities. The fluid flows from the interior of the balloon are thus generally directed perpendicularly to the interior surfaces of the body cavity and are sometimes pressurized so that any medication contained in the fluid will forcefully impact the interior walls of the cavity. These fluid streams can only clean areas similar to the cross-sections of the streams and schemes for moving the streams over the side walls invariably leave some areas untouched or under cleaned. Increasing the force of the streams impacting the walls may do harm to the walls.

In many medical situations it is desirable to remove dead cells and the like which may have accumulated on the interior wall of a body cavity. For example, in a healthy nose mucus produced by the lining of the paranasal sinuses drains out of the sinus through the ostium, an opening connecting the interior of the sinus cavity to the nasal passages, carrying cellular and bacterial debris with it. In conditions such as sinusitis the mucus may be prevented from freely exiting the ostium and tends to accumulate the debris on the interior walls of the sinus cavities interfering with the normal functions and healing of the cavities. This mucosal congestion may result in microbial growth on the surface which must be removed to restore the sinuses to their normal function.

SUMMARY OF THE INVENTION

The present invention is accordingly directed toward methods and apparatus to irrigate, with or without medication, to scrub, clean, and/or debride the interior surfaces of infected body cavities or body cavities suffering from accumulations of dead cells, mucous, bacteria accumulations or the like to restore them to a healthy condition. This is preferably done by a fluid flow in a direction generally parallel to the cavity wall to scrub the wall without imposing forces that may harm the wall.

Very broadly the method and apparatus comprises a balloon which may be inserted in deflated condition through the ostium of the cavity to be treated and then inflated to produce restricted passages between the complementary walls of the balloon and body cavity. A pressurized fluid flow is then introduced into the area between one end of the balloon, preferably the distal end, considering the ostium end to be the proximal end. This fluid flow passes over the outer sides of the balloon through the restricted passage. At the other end of the balloon, preferably near the ostium, an outflow tube, which may be negatively pressurized, sucks out the fluid, as well as any debris picked up by the fluid flow over the interior walls of the cavity, such as cellular debris and the like. In other embodiments the fluid flow out of the cavity may be under the force of gravity and/or the pressure of the inflowing fluid. This fluid flow along the interior walls of the cavity has many advantages over devices that direct the fluid flow perpendicularly against the walls. First, pointing a forceful stream at the inner wall of the cavity is inefficient. First, the stream pointed more or less perpendicular to the wall cleans only an area more or less the cross sectional area of stream. Repeated movement of the stream, crisscrossing the inner surface area over and over again is problematic that the walls can be completely scrubbed clean. Also in some cases the force of the stream impacting the wall may be increased to a point that the wall itself is injured. A flow of cleaning fluid that runs parallel to the wall is a far more thorough and efficient means of scrubbing the interior wall of a cavity with a greater freedom to increase pressures without destroying the interior wall.

Second, soon after liquid is forced into a cavity the cavity will fill and the effect of the stream is dissipated by the inertia of the liquid in the cavity. To push a relatively thin stream into a filled cavity, no matter how large the outflow, produces a languid flow across/parallel to the cavity inner surface.

In one embodiment of the invention, which will be subsequently disclosed in detail, the inflow tube passes through the center of the balloon and the central passage through the balloon is sealed against the outer wall of the inflow tube, in the manner of a Foley Catheter. In this embodiment, when the balloon is in a collapsed condition, it may be inserted through the ostium, into the cavity, by passing the inflow tube into the cavity. The output end of the inflow tube projects beyond one end of the balloon. This arrangement resembles a Foley Catheter.

In another embodiment the balloon will have irregular projections extending from its outer surface which will contact the interior walls of the cavity and create interrupted passages between the outer wall of the balloon and the interior wall of the cavity. Fluid, which may be medicated, is then introduced through an inflow tube which extends through the center of the balloon and terminates at the distal end of the cavity. Pressurized fluid flow is then passed through the inflow tube and directed by a nozzle at the end of the tube against a deflecting structure, preferably supported on the distal end of the balloon, which directs the flow from the tube into the passage between the balloon exterior and the interior wall of the cavity.

The irregularities on the balloon prevent direct flow out of these passages and continually deflect the fluid stream laterally, parallel to the cavity wall in such a way as to achieve turbulent or near turbulent conditions in the fluid. The flow will debride contaminating elements on the interior wall of the cavity and carry them to the proximal end of the balloon and of the cavity where they are drawn through outflow tubes, preferably with an active suction pressure exerted on the tubes.

The balloon may have radically extending corrugations on its outer surface to aid in creating turbulence or near turbulence in the fluid flow.

In certain embodiments of the invention which will be subsequently disclosed in detail the cross sectional shape of the protuberances that project from the sides of the balloon will be such as to induce turbulence or near turbulence in the fluid flow. Turbulence is also a function of the dimensions of the device and the viscosity and flow rate of the fluid. Turbulence will greatly aid the debriding action. The surface of the balloon may have dimples or indentations to affect flow towards a turbulent nature.

In other embodiments of the invention the outer surface of the balloon will carry a resilient deflecting cowling which will lie flat over the exterior of the balloon when it is collapsed over the inflow tube and when the balloon is inflated one end of the cowling will project outwardly toward the interior of the cavity at an angle toward the ostium to aid the deflection of the flow through the cavity.

In one embodiment of the invention the exterior side of the balloon supports a planar raceway which spirals toward the ostium end of the cavity when the balloon is inflated. This raceway forces the input fluid to traverse a longer path than it would if it could flow directly toward the ostium end of the passage between the exterior of the balloon and the interior wall of the cavity. This increases the flow rate of the fluid after it exits the input tube and improves the ablating force against the cavity interior, as well as elongate the flow path to increase the cleaning action.

In some embodiments of the invention a concave deflector is supported above the output end of the input flow tube so as to deflect the flow around the sides of the balloon. This deflector may be supported on the flow tube by umbrella-like ribs which allow the deflector to fold along the sides of the outflow tube during insertion of the tube and the deflated balloon through the ostium of the body cavity. Once in the cavity, the deflector may be opened up either by a spring mechanism or the force of the outflow from the tube. Alternatively, the deflector may be moved between its folded and unfolded position by the manipulation of cords or the like which may be controlled from the exterior of the cavity. The deflector may have a number of holes in its surface to allow the fluid flow to irrigate the area of the cavity wall covered by the deflector.

In still another embodiment of the invention the walls of the balloon may be formed with pores or of a porous material. In this embodiment the incoming fluid flow, or at least a portion of it, is directed to the interior of the balloon so that it passes through the pores under the inflow pressure and irrigates the walls of the cavity and may additionally interact with the fluid flow between the cavity and balloon walls to assist in the creation of turbulence in that fluid flow.

The fluid flow is preferably arranged so that it achieves turbulence, or near turbulence which acts to scrub the interior walls of the body cavity as the fluid flows through the channels between the opposed walls of the balloon and the cavity. In the embodiments with protuberances extending from the balloon toward the wall of the cavity, the shape and position of these protuberances, as well as indentations of the balloon wall, may be such as to influence the flow toward turbulence.

BRIEF DESCRIPTION OF THE DRAWINGS

Other objects, advantages, and applications of the present invention will be made apparent by the following detailed description of preferred embodiments of the invention. The description makes reference to the accompany drawings in which.

DETAILED DESCRIPTION OF THE PREFERRED EMBODIMENTS

While the present description of the invention deals with the paranasal sinuses as the body cavities to be treated, it should be understood that the method and apparatus of the present invention have application to other body cavities and passages such as arteries, naso-lachrymal ducts, eustachian tubes, or the like and the present description should not be viewed as limited to the paranasal sinuses.

The paranasal sinuses are prime examples of the type of body cavities that may be treated using the methods and apparatus of the present invention because they are lined with mucus-producing tissue which normally drains out of each sinus under gravity forces but in certain cases this drainage does not operate properly and the openings between the sinuses and the connecting nasal passages may become blocked, leading to congestion of the sinuses and potential microbial growth which can produce a sinus infection. The mucosal linings of the cavity become contaminated with both live and dead bacteria and other debris. Removing this debris may be a first step in curing the infection.

Figure 1:
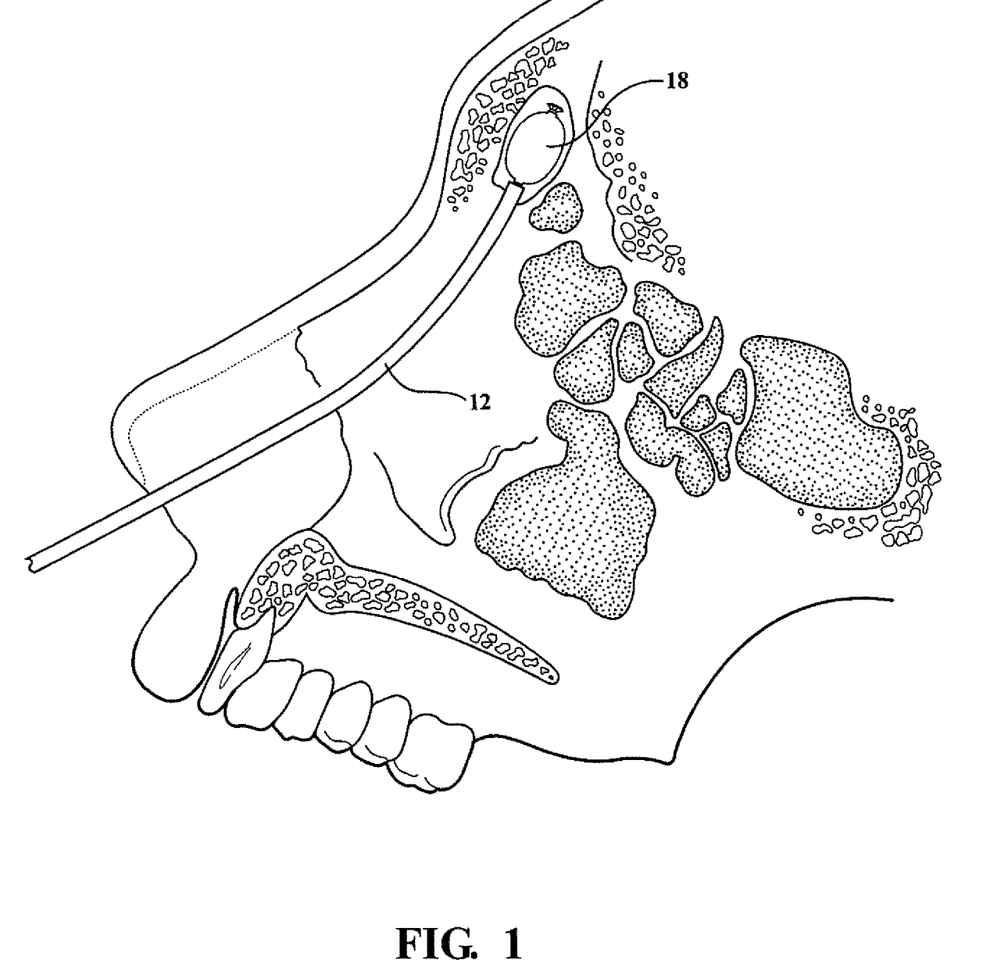
FIG. 1 is a cross-sectional view through the upper forward portion of a human skull illustrating a device formed in accordance with the present invention for irrigating a paranasal sinus of the person.

Referring to FIG. 1, the method and apparatus of the present invention is directed toward irrigating, for the purpose of debriding and cleaning the interior surface of a body cavity such as a paranasal sinus 10. Essentially, the invention comprises a fluid inflow tube 12 which carries a balloon 18 which may be inserted into the cavity 10 through its ostium while the balloon is in a deflated condition, and then air and/or fluid flow through the tube 12 inflates the balloon 18 to create a narrow passage between the exterior of the balloon and the interior wall of the cavity. A fluid inflow through the tube 12 then exits the balloon as will be subsequently detailing and moves forcefully against the interior wall of the cavity to perform the cleaning and debriding operation.

Figure 2:
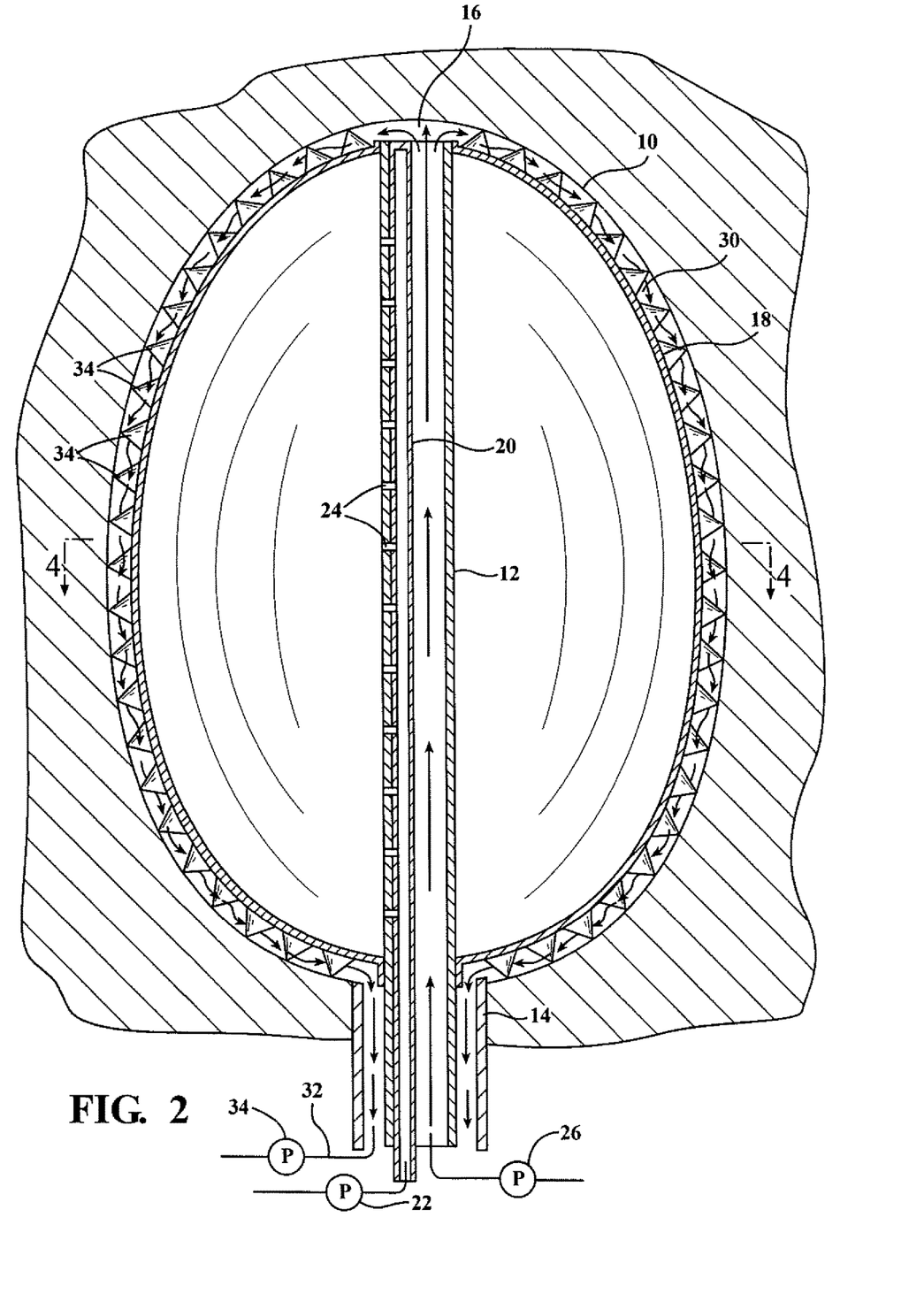
FIG. 2 is an enlarged cross section of a body cavity having its inner wall being irrigated by a first embodiment of a device formed in accordance with the present invention.

Referring to FIG. 2, which constitutes a cross section through the paranasal cavity 10, an instrument which practices the method of the present invention comprises an inflow or irrigation tube 12 which is adapted to pass through the ostium 14 of the cavity 10 so that a first end of the irrigation tube is outside of the cavity and a second end terminates in an open end 16 of the tube which may be positioned near the distal end of the cavity 10 with respect to the ostium.

The tube 12 passes through a central cavity in a balloon 18 which is shown in inflated condition. The wall of the central cavity is secured to the outer wall of the tube 12 as in a Foley Catheter. The distal end 16 of the tube 12 extends beyond the balloon 18 and the proximal end of the tube 12 extends through the ostium 14 to the exterior of the cavity.

An inflation tube 20 which is formed about the outer wall of the tube 12 extends through the ostium and carries air from a pump 22 into the balloon 18, through side ports 24, in order to inflate the balloon after it has been inserted into the cavity through the ostium. A second pump 26 is connected to the inlet or irrigation tube 12 at the proximal end. It acts to pump fluid from any appropriate source (not shown) through the tube 12 and out the open distal end 16 at the far end of the cavity 10. The output end 16 of the input tube 12 may be fitted with an appropriate nozzle, spray head, or the like (not shown) or it may simply be left open in certain embodiments.

The flow from the output 16 of the tube 12 passes through the relatively narrow passage 30 defined by the inner wall of the body cavity 10 and the outer wall of the balloon 18. The flow extends downwardly in the drawing of FIG. 2 until it reaches the area of the ostium which it may pass through by gravity and the force of the input flow, or alternatively exit the cavity 10 through a suction passage 32 which is evacuated by a pump 34.

Depending upon the inflow rate through the tube 16, the viscosity of the fluid being pumped through the tube, and physical dimensions of the apparatus, the fluid flow may achieve turbulence at various points during its passage. The turbulence aids in scouring any debris from the inner wall of the body cavity 10. A nonturbulent or laminar flow will also act to debride material from the inner wall of the cavity. The balloon 18 may be inflated to a condition wherein its outer surface is somewhat flaccid and deforms under the fluid flow forces, which will assist in the creation of a turbulent flow in certain geometries.

A plurality of protuberances 34 spaced over the exterior of the balloon may contact the inner walls of the cavity 10 to assist in spacing the outer surface of the balloon with respect to the inner wall of the cavity or, in alternative embodiments, the outer ends of the projections 34 may be spaced from the inner wall of the cavity when the balloon is in its inflated condition.

Figure 7:
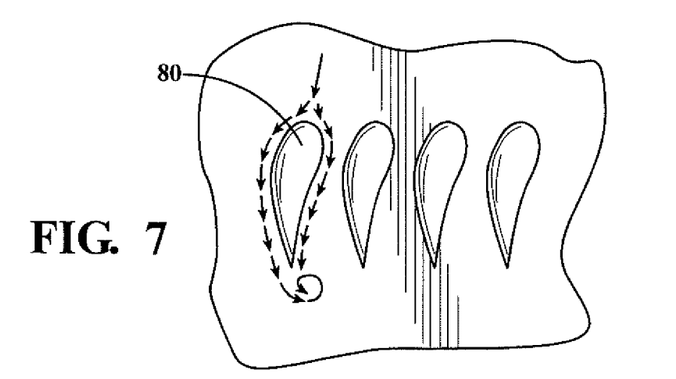
FIG. 7 is an enlarged cross section of one form of a protuberance formed on the balloon exterior.

The protuberances are spaced along the outer surface so that there is no clear path for the fluid to flow through the channel 30, but rather the protuberances deflect the flow laterally, increase the speed of the flow, and in certain situations may bring the flow to a turbulent state. The cross sections of the protuberances 34 may be airfoil shaped or the like, as shown in FIG. 7, to increase the speed of a flow over their surfaces and promote turbulence at their trailing edges.

At the far end of the flow path, adjacent to the ostium 14, the output flow may be pressurized by the suction pump 36 or, in some embodiments, it may simply flow out of the ostium under gravity forces and/or the pressure of the incoming flow.

In use, the balloon 18 is initially deflated so that it lies closely along the exterior of the inflow tube 12 and may be inserted into the body cavity 10 through the ostium 14, with the tube. The balloon may then be inflated by air or other gas through the pump 22 and the tube 20. The gas will flow outwardly into the interior of the balloon through the ports 24. The balloon 18 may be inflated until the extending edges of the projections 34 contact the inner wall of the cavity 10 or, to a lesser degree, allowing a larger free channel 30 for fluid flow. Fluid is then forced through the inflow tube 12 by the pump 26 and exits into the channel 30 through the top 16 of the inflow tube 12. The fluid is forced through the channel 30 which surrounds the balloon and scours the inner walls of the cavity 10 to remove any loose material such as dead cells, accumulated mucus, and the like. This material is then carried out the ostium through the fluid forces and gravity or alternatively through the channel 32 based on the vacuum created by the pump 36. After the irrigation is completed, the balloon may be deflated by reversing the pump 22 and then the inflow tube 12, with the collapsed balloon draped over its surface, may be withdrawn through the ostium 14.

Figure 3:
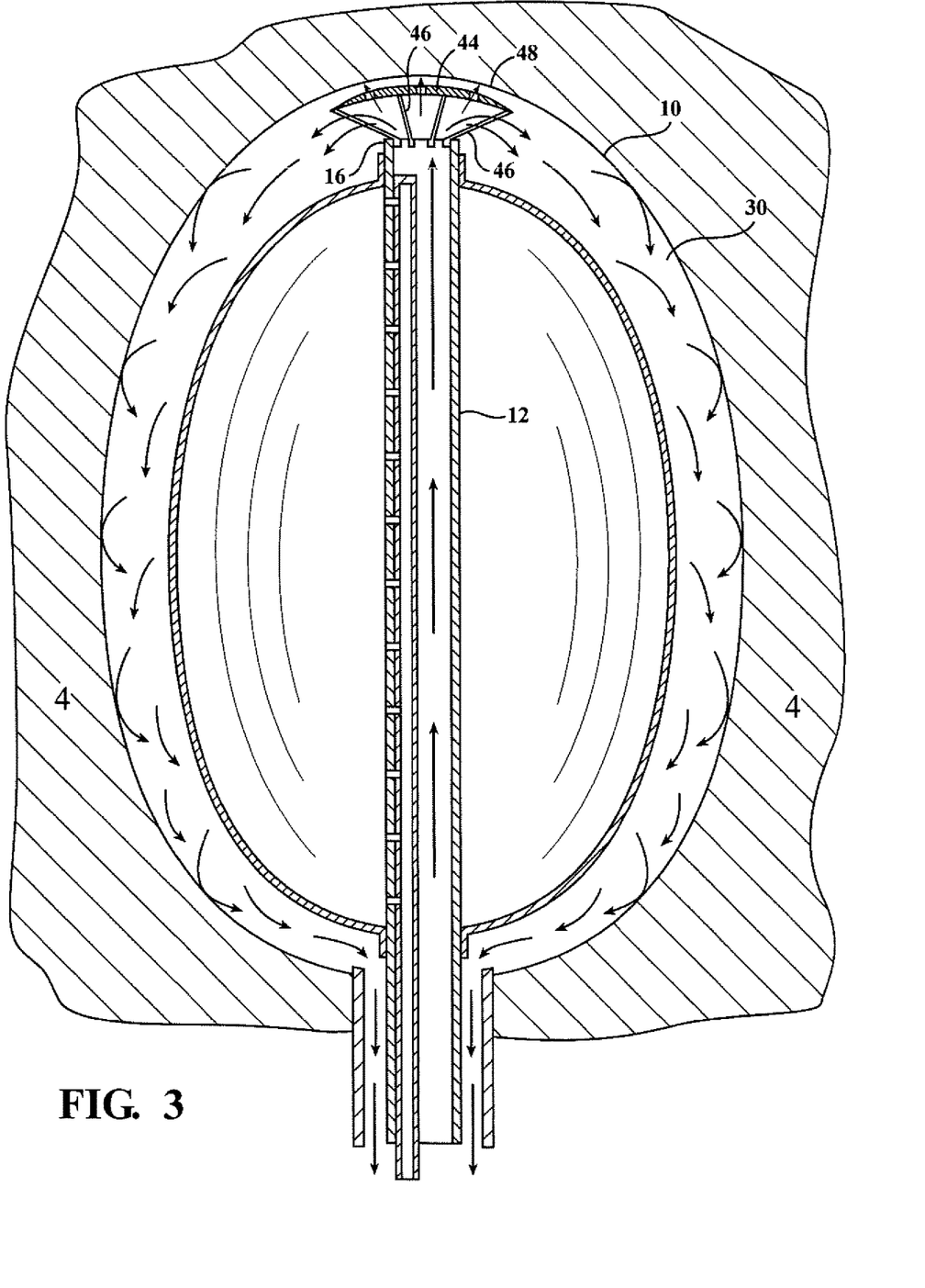
FIG. 3 is a cross section through the device and cavity of FIG. 3 taken along lines 4-4 of FIG. 3.

FIG. 3 is a cross-sectional view through the embodiment of FIG. 2, taken along line 4-4 of FIG. 2. The arrows illustrate the transverse pattern of the fluid flow as a result of interference between the otherwise downward flow toward the ostium, wherein the lateral movement is forced by the interference between the flow and the projections 34.

Figure 4:
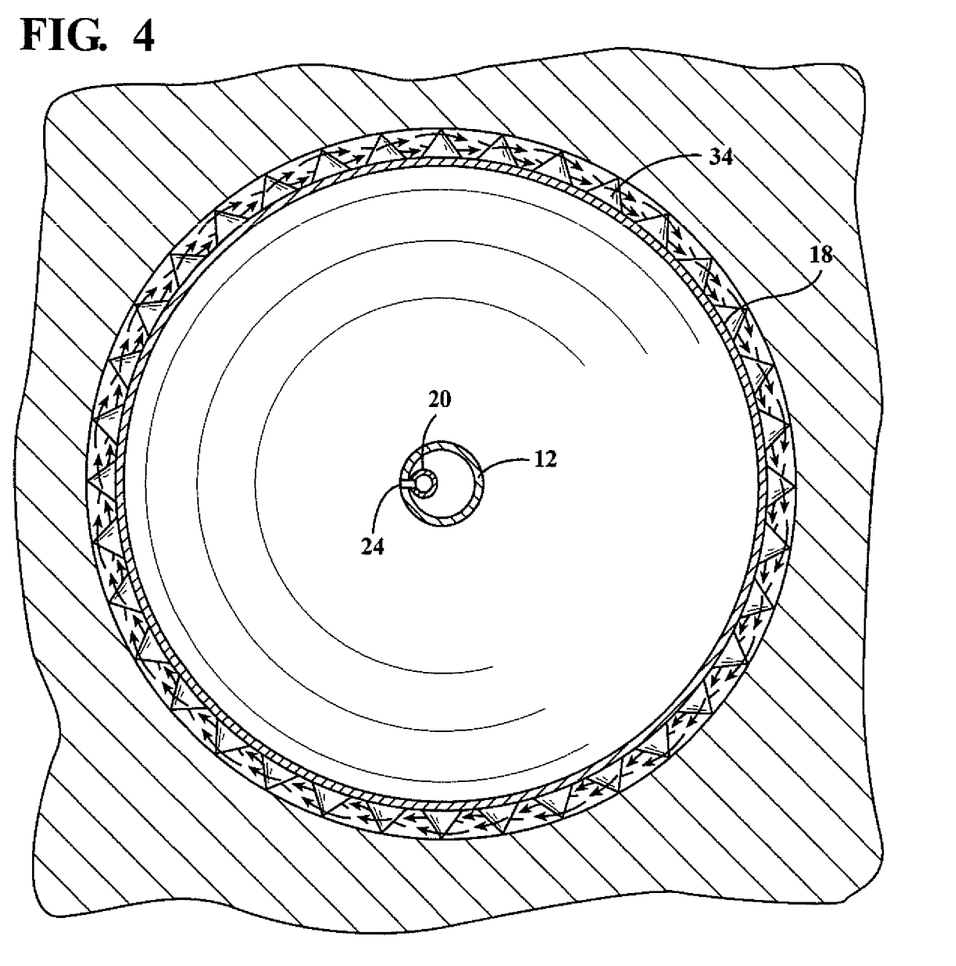
FIG. 4 is a cross-sectional view like FIG. 2, illustrating an alternative embodiment of the invention which includes a deflector disposed at the output end of an inflow tube in order to direct the flow through the passage between the exterior of the balloon and the interior wall of the cavity.

FIG. 4 illustrates an alternative form of the invention which includes a foldable deflector 44 supported on the output end 16 of the inflow tube 12. In this embodiment the same numbers are applied to the components to the extent they are identical to the components of the embodiment of FIG. 2.

The deflector is a thin, concave shell which extends to a form parallel to the inner wall 10 of the cavity, at the end of the cavity opposite to the ostium. It may be formed of a flexible material. The deflector 44 is supported on the end 16 of the input tube by means of ribs 46 which preferably have one end pivotably attached to the end 16 of the inflow tube and their other ends pivotably attached to the shell 44 at spaced points. The deflector 44 may be moved to a collapsed form wherein it lies along the sides of the distal end of the tube 12 for insertion and removal of the tube through the ostium. It preferably has a plurality of holes 48 in its surface to allow the flow from the output of the tube 12 to move against the inner wall of the cavity 10 on the convex side of the deflector. The deflector forces the flow from the output end 16 of the tube 12 along the sides of the balloon through the channel 30.

In the embodiment of FIG. 4 there are no projections 34 extending from the surface of the balloon, but the input flow rate is such as to force the flow against the inner wall 10 of the cavity at speeds which may achieve turbulence to aid the scouring action. Since there are no projections from the outside of the balloon, the balloon may be inflated into closer proximity to the wall 10 of the cavity than the embodiment of FIG. 2.

The deflector 44 may normally assume its collapsed condition about the exterior of the tube 12 through use of biasing means such as a spring (not shown). It may then be forced open by the flow out of the end 16 of the tube 12. Alternatively, it may normally be biased toward an extended position and cables or the like (not shown) may be passed through the tube 12 from the exterior of the cavity 10 to the deflector 44 to force it into a folded condition.

Figure 5:
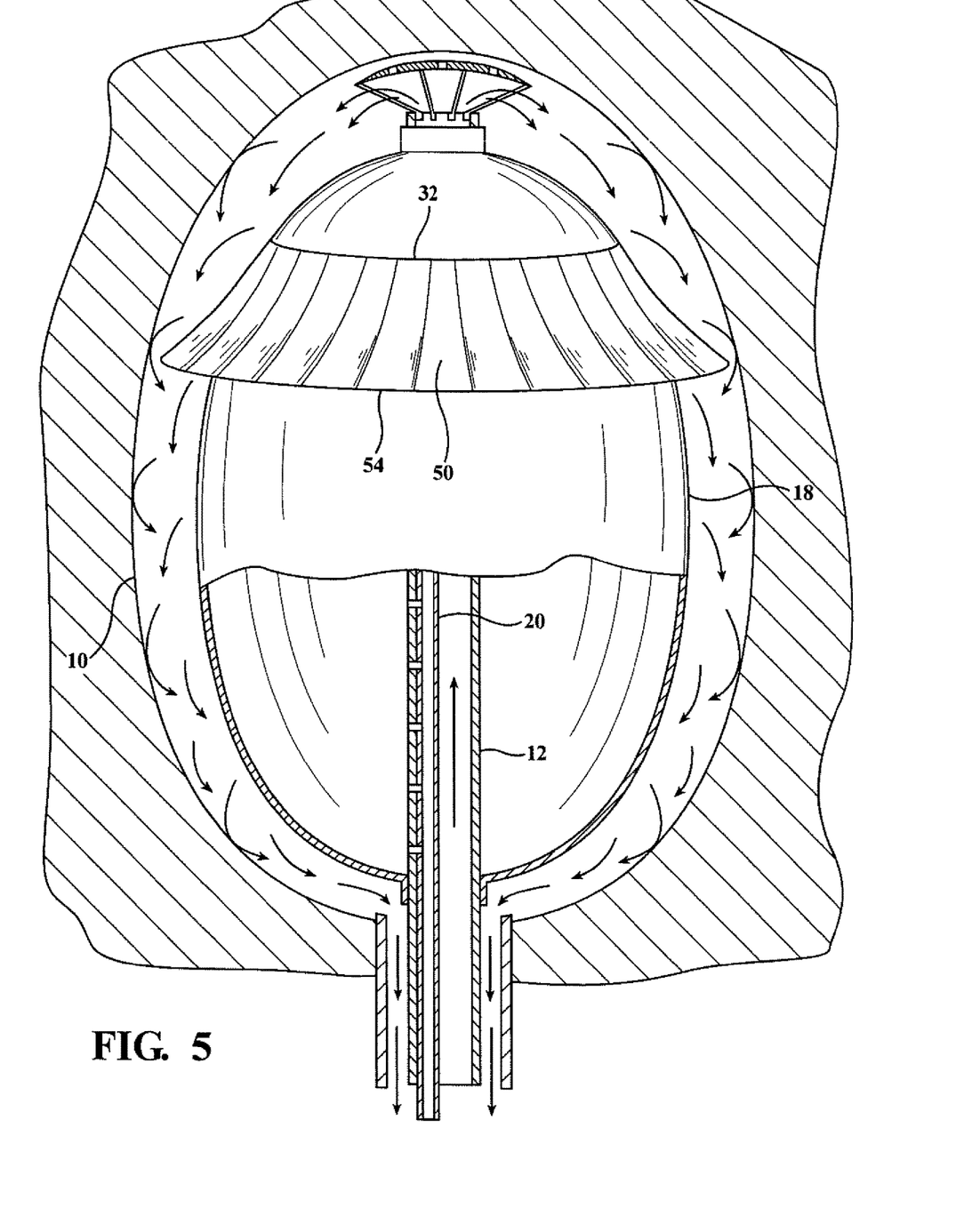
FIG. 5 is a cross section through a body cavity employing an alternative embodiment of the invention which comprises an extending canopy for aiding and directing the fluid flow against the interior walls of the cavity.

FIG. 5 illustrates another embodiment of the invention, much like the embodiment of FIG. 3, but further including a canopy 50 which has one end 52 attached to the exterior of the balloon and the other end free of the balloon. The canopy 50 may be normally biased so as to lie over the surface of the balloon 18 for insertion and removal of the apparatus through the ostium 14. Once in the cavity, and after the balloon is inflated through the tube 20, the lower end 54 of the canopy 50 may be shaped to extend outwardly toward the side walls of the cavity and force the fluid flow against the side walls 10 of the cavity. By narrowing the resulting passage between the exterior of the balloon and the interior of the cavity, the flow is accelerated and may attain turbulence at certain points of its path.

Figure 6:
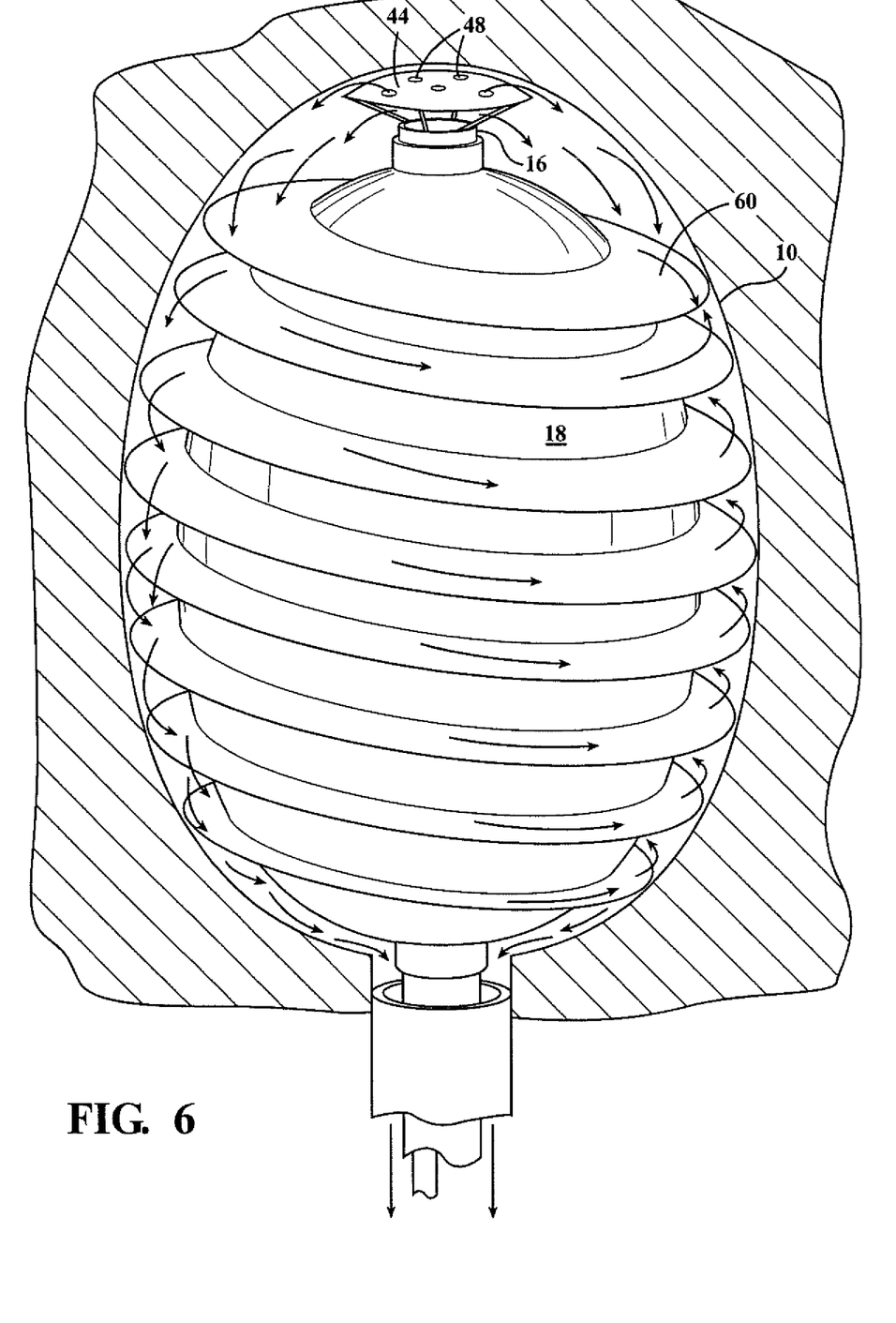
FIG. 6 is a similar cross-sectional view through an alternative embodiment of the invention having a spiral canopy supported on its exterior surface to accelerate the fluid flow and drive it against the interior walls of the cavity.

FIG. 6 discloses another embodiment of the invention, similar to the embodiment of FIG. 5, with the exception that instead of having a single canopy 50 encircling the balloon, as illustrated in FIG. 5, a spiral canopy 60 extends along the entire height of the balloon 18. The output flow from the deflector 44 is directed against the top section of the spiral canopy 60 and the edges of the canopy 60 extend close to the inner walls of the cavity 10. The flow is forced to follow the spiral path created by the canopy 60 and the fluid flow forces the flow to attain a high speed along the spiral path, heightening the ability to achieve turbulence in the flow.

Alternatively, the canopy 60 could take the form of separate closed rings extending around the perimeter of the balloon 18, rather than a closed spiral track 60. These rings would create a corrugated pattern that would force the flow through the channel 12 to move back and forth laterally while still moving from the outlet 16 to the ostium, increasing the scouring action.

The protuberances 34 illustrated in the embodiments of FIG. 2 and FIG. 4 may be used in any of the embodiments and may be arranged in the shape of an airfoil, as illustrated in FIG. 7 at 80, to enhance the turbulence of the fluid.

Having thus described my invention, I claim:

1. A method of irrigating the interior surface of a body cavity having an ostium connecting the interior of the cavity with an adjacent body passage, comprising:
    inserting an inflatable balloon, in a deflated condition, through the ostium into the interior of the cavity;
    inflating the balloon;
    wherein the balloon contains a series of projections formed on its outer surface, and wherein the projections are adapted to contact the interior wall of the cavity when the balloon is inflated to form a passage between the exterior wall of the balloon and the interior wall of the cavity;
    while the balloon remains inflated, introducing a fluid flow into the passage through an inflow tube extending between the exterior of the ostium and through a central passage of the balloon to an output at the end of the body cavity opposite to the ostium;
    wherein the projections interfere with the fluid flow in such a way as to urge the fluid flow into a turbulent condition;
    removing the fluid from the passage through an outflow tube having one end connecting to the passage at the ostium end of the passage and the other end terminating exterior of the ostium; and
    deflating and removing the balloon.

2. The method of claim 1, wherein the fluid flow is operative to debride debris collected on the interior wall of the cavity.

3. The method of claim 1, wherein the fluid contains medication which is applied to the interior wall of the body cavity.

4. The method of claim 1, wherein the fluid flow through said passage between the interior wall of the cavity and the exterior wall of the balloon achieves turbulence.

5. The method of claim 1 further comprising expelling the fluid flow from the output end of the inflow tube against a deflector shaped to direct the fluid flow through the passage between the interior wall of the cavity and the exterior wall of the balloon.

6. The method of claim 5, wherein the deflector at the output of the inflow tube has holes formed in its surface to allow irrigation of the interior wall of the cavity generally shielded from the output flow by the deflector.

7. The method of claim 5, wherein the deflector is movable between an extended and a retracted position and is resiliently urged toward the extended position by resilient means extending between the deflector and the inflow tube, and may be retracted for insertion and retraction through the ostium by elongated control elements each having one end connected to a section of the deflector and extending through the inflow tube to allow their manipulation from the exterior of the ostium.

8. The method of claim 7, wherein the deflector is moved between its retracted position and its extended position under the force of the flow from the output of the inflow tube.

9. The method of claim 1, wherein the projections are spaced over the exterior wall of the balloon so that when inflated, the passage between the interior wall of the body cavity and the exterior wall of the balloon is obstructed by the projections forcing the fluid flow through the passage to move in transverse directions.

10. The method of claim 1, wherein the projections have an airfoil shape in a cross section extending parallel to said passage.

11. The method of claim 1 in which the balloon in its inflated condition is flaccid and ripples under the force of the inflow fluid to induce the fluid motion toward turbulence.

\* \* \* \* \*